(12) United States Patent
Lawrence

(10) Patent No.: US 6,300,629 B1
(45) Date of Patent: *Oct. 9, 2001

(54) DEFECT REVIEW SEM WITH AUTOMATICALLY SWITCHABLE DETECTOR

(75) Inventor: Bradley Lawrence, Cupertino, CA (US)

(73) Assignee: Applied Materials, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/164,230

(22) Filed: Sep. 30, 1998

(51) Int. Cl.[7] ................................. G01N 23/225
(52) U.S. Cl. ............................ 250/310; 250/397
(58) Field of Search ..................... 250/310, 397

(56) References Cited

U.S. PATENT DOCUMENTS

| | | | |
|---|---|---|---|
| 4,560,872 | * 12/1985 | Antonovsky | 250/310 |
| 4,831,266 | 5/1989 | Frosien et al. | 250/310 |
| 5,043,583 | * 8/1991 | Robinson | 250/363.01 |
| 5,424,541 | 6/1995 | Todokoro et al. | 250/310 |
| 5,466,940 | 11/1995 | Litman et al. | 250/397 |
| 5,608,218 | * 3/1997 | Sato | 250/310 |
| 5,644,132 | * 7/1997 | Litman et al. | 250/310 |
| 6,084,238 | * 7/2000 | Todokoro et al. | 250/310 |

* cited by examiner

*Primary Examiner*—Bruce Anderson
(74) *Attorney, Agent, or Firm*—McDermont Will and Emery

(57) ABSTRACT

A method and apparatus is provided for imaging of topographic and material features of defects on the surface of a semiconductor wafer with simultaneous display of multiple SEM images generated by a single detector of backscattered and secondary electrons. A primary beam is directed at a specimen to release secondary electrons therefrom and to backscatter electrons of the particle beam therefrom, which electrons are detected by a single detector, while an imager produces and displays images responsive to the detector, and an electrode directs the path of the secondary electrons. A charge controller controls the charge placed on the electrode such that the imager produces a plurality of different images desired by the user, which are displayed substantially simultaneously by the imager. This enables inspection of a location of interest on the surface of a wafer using several images, each image possibly having different attributes, thereby facilitating comparison of images of defect sites and reference sites, identification of defects, and classification of defects.

15 Claims, 6 Drawing Sheets

DEFECT REVIEW SEM WITH AUTOMATICALLY SWITCHABLE DETECTOR

FIELD OF THE INVENTION

The present invention relates to particle beam imaging and measurement equipment, such as a scanning electron microscope. The invention has particular applicability for in-line inspection of semiconductor wafers during manufacture of high-density semiconductor devices with submicron design features.

BACKGROUND ART

Current demands for high density and performance associated with ultra large scale integration require submicron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

Conventional in-process monitoring techniques employ a particle beam apparatus, such as a scanning electron microscope (SEM), for defect review. The SEM scans the surface of a specimen with an energetic particle beam; e.g., an electron beam having an energy of about 400 eV to about 1 keV. The impact of the particle beam on the surface of the specimen causes electrons of the particle beam to be deflected, or "backscattered", by atoms of the specimen with energies close to that of the particle beam (i.e., about 400–1000 eV). These deflected electrons are referred to as backscattered electrons. Electrons released from the surface of the specimen due to the impact of the particle beam, with energies of about 50–100 eV, are referred to as secondary electrons. It is well known that since the backscattered electrons are deflected by atoms of the specimen, they provide information relating to the material composition of the specimen (e.g., density information). On the other hand, the secondary electrons are released from the specimen corresponding to the slope of the surface of the specimen, so secondary electrons provide topographical information, i.e., the distribution of secondary electrons will vary with the slope of the surface of the specimen. Thus, images of a semiconductor wafer under review showing material contrast can be generated after detecting backscattered electrons, and images of the wafer showing the bottoms of trenches and contact holes, as well as particles and other surface features, can be generated after detecting secondary electrons. Furthermore, certain attributes of a defect may be apparent only in an image generated by a mix of both backscattered and secondary electrons.

FIG. 1 depicts a prior art SEM for producing such images, wherein a primary beam 11 is directed at a wafer 12 to produce backscattered electrons BSE and secondary electrons SE, which are detected by a single detector 13. Backscattered electrons BSE tend to deflect from wafer 12 at acute angles, while secondary electrons SE are dispersed at many angles. Secondary electrons SE which impinge detector 13 simultaneously with backscattered electrons BSE are selectively repelled by an electrode in the form of a grid 14 provided near the entry side of detector 13 to produce the desired images of wafer 12.

In practice, a switch 15, typically a potentiometer, is manually adjusted to negatively bias grid 14 such that an image of the desired combination of backscattered and secondary electrons is produced. For example, a negative potential of about the same energy as secondary electrons SE is applied to grid 14 via switch 15 to repel most secondary electrons SE, thus allowing easier detection of backscattered electrons BSE, which are not significantly repelled by the negative bias on grid 14 because they are of a substantially higher energy. Then, grid 14 is switched off and an image is generated from secondary electrons SE, since when grid 14 is not biased, mostly secondary electrons impinge on detector 13.

The detection apparatus of FIG. 1 suffers from the disadvantage of not providing simultaneous viewing of images generated as a result of the detection of backscattered electrons BSE and secondary electrons SE; that is, the two or more respective images are normally produced sequentially (by varying the potential on grid 14), so that only one image can be seen by the operator at a time.

SUMMARY OF THE INVENTION

Simultaneous viewing of several images would provide information regarding different attributes of a specimen. For example, one image may show material characteristics, another may show topographical features of a given site on a wafer, and still another a combination of attributes. Simultaneous viewing would facilitate comparison of images of defect sites and reference sites, identification of defects, and classification of defects, since attributes of a defect may appear in one type of image and not in any other. There exists a need for a SEM having a single detector which simultaneously displays images generated from the detection of backscattered and secondary electrons.

According to the present invention, the above stated needs and others are met by a particle beam apparatus for imaging of a specimen, the particle beam apparatus comprising a particle source for providing a primary beam for impinging on the specimen to release secondary electrons therefrom and to provide backscattered electrons to be deflected by the specimen; a detector for detecting the backscattered and the secondary electrons; an electrode disposed between the detector and the specimen chargeable to a plurality of potentials for directing a path of the secondary electrons; an imager responsive to the detector for generating images based on the secondary electrons and the backscattered electrons; and a charge controller for automatically controlling the potential on the electrode such that the imager simultaneously generates a plurality of different images.

Another aspect of the present invention is a method for imaging a specimen, which method comprises directing a particle beam onto the specimen to release secondary electrons therefrom and to deflect backscattered electrons of the particle beam therefrom; detecting the backscattered and the secondary electrons; directing the path of the secondary electrons relative to the detector; consecutively producing a plurality of images based on the detected electrons; and displaying the plurality of images substantially simultaneously.

Additional features and advantages of the present invention will become readily apparent to those skilled in this art from the following detailed description, wherein only the preferred embodiment of the invention is shown and described, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Conventional single-detector semiconductor wafer review SEM's do not provide simultaneous viewing of multiple images produced from backscattered electrons, secondary electrons, and combinations thereof. Moreover, to change the viewed image, the conventional apparatus must be manually adjusted such that an image of the desired combination of backscattered and secondary electrons is produced. The present invention addresses and solves these problems by simultaneously providing a plurality of different images based on information provided by backscattered and secondary electrons, thereby facilitating comparison of images of defect sites and reference sites, identification of defects, and classification of defects.

According to certain embodiments of the present invention, a primary beam is directed at a wafer to release secondary electrons therefrom and to provide electrons to be backscattered therefrom, which backscattered and secondary electrons are then detected by a single detector. An imager produces and displays images responsive to the detector, and an electrode for directing the path of the secondary electrons is positioned at the entry side of the detector. A charge controller controls the charge placed on the electrode such that the imager produces a plurality of different images desired by the user, which are displayed substantially simultaneously. The present invention enables inspection of a location of interest on the surface of a wafer using several images, each having different attributes; e.g., a backscattered electron image most indicative of material characteristics, and a secondary electron image most indicative of topography, thus facilitating tracing the causes of defects to their source, such as to a particular process step or even to a particular piece of processing equipment.

Figure 1:
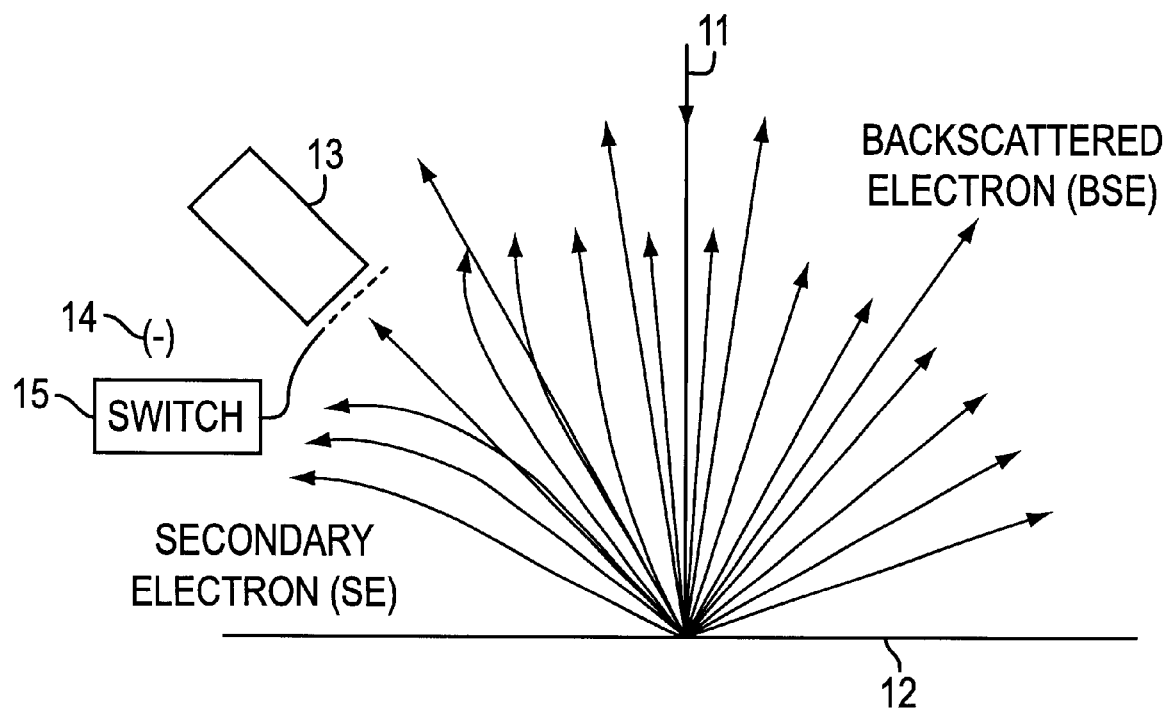
FIG. 1 depicts a conventional SEM.
Figure 2:
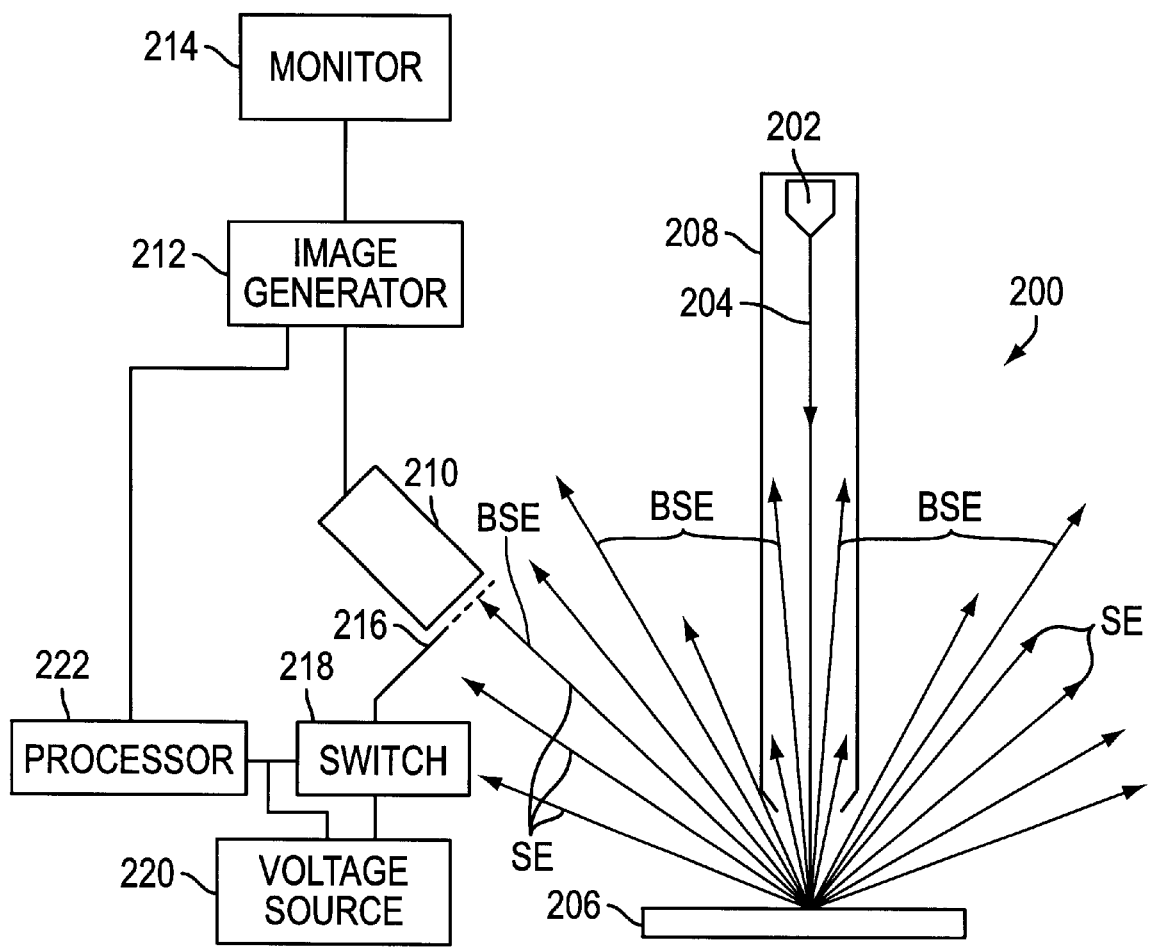
FIG. 2 depicts a SEM according to an embodiment of the present invention.

An apparatus according to an embodiment of the present invention is illustrated in FIG. 2. A particle beam apparatus 200 comprises a particle source 202 for scanning the surface of a specimen 206, such as a semiconductor wafer, with a primary beam 204 enclosed and focussed within an optical column 208. Particle source 202 is preferably a field-emission electron source characterized by virtual source size of several nanometers and an energy spread of several tenths of an electron volt. Electrons of primary beam 204 typically impinge on specimen 206 with a kinetic energy of about 400 eV to about 1000 eV, referred to as the "landing energy" of primary beam 204.

Primary beam electrons impinge on specimen 206 and are deflected (backscattered) by atoms of specimen 206 with a kinetic energy close to the landing energy of primary beam 204 to provide backscattered electrons BSE. Impinging electrons of primary beam 204 also cause secondary electrons SE having a kinetic energy significantly below the landing energy of primary beam 204; e.g., about 50 eV to about 100 eV, to be released from the surface of specimen 206. Primary beam 204 preferably has a higher flux than typical prior art single-detector SEMs, to raise the number of electrons SE, BSE, thereby improving the clarity of the resultant images. The flux increase is preferably accomplished by raising the primary beam current above conventional amperage levels while keeping the primary beam voltage at typical prior art levels to maintain a conventional acceleration voltage (i.e., the acceleration with which electrons from primary beam 204 impinge on specimen 206).

A detector 210, such as a microchannel plate detector or a scintillator detector, is located external to column 208 enclosing primary beam 204. The detector 210 operates to detect backscattered electrons BSE and secondary electrons SE. An image generator 212, such as an electronic computer, receives signals from detector 210 and produces images based on the detected backscattered electrons BSE and secondary electrons SE. The images are displayed on monitor 214, such as a cathode ray tube (CRT).

An electrode 216, electrically chargeable for directing the path of secondary electrons SE, is disposed between detector 210 and specimen 206, preferably proximal to detector 210. Electrode 216 is preferably in the form of a grid, and is chargeable to positive or negative potentials including the kinetic energy of the secondary electrons SE. The potential on electrode 216 is controlled by a charge through switch 218, which connects the electrode 216 to receive power from voltage source 220. Processor 222, such as an electronic computer, functions as a charge controller along with switch 218. Processor 222 directs switch 218 and voltage source 220, as by an algorithm, to control the duration, magnitude and polarity of the charge on electrode 216, such that image generator 212 consecutively produces a plurality of different images based on backscattered electrons BSE and secondary electrons SE, as specified by the user. Image generator 212 causes monitor 214 to display the plurality of different images simultaneously, as on a "split-screen" image. Alternatively, multiple screens may be employed and separately provided with one of the multiple images. Furthermore, additional detectors 210 and electrodes 216 can be employed to obtain additional images from other perspectives simultaneously.

Figure 3A:
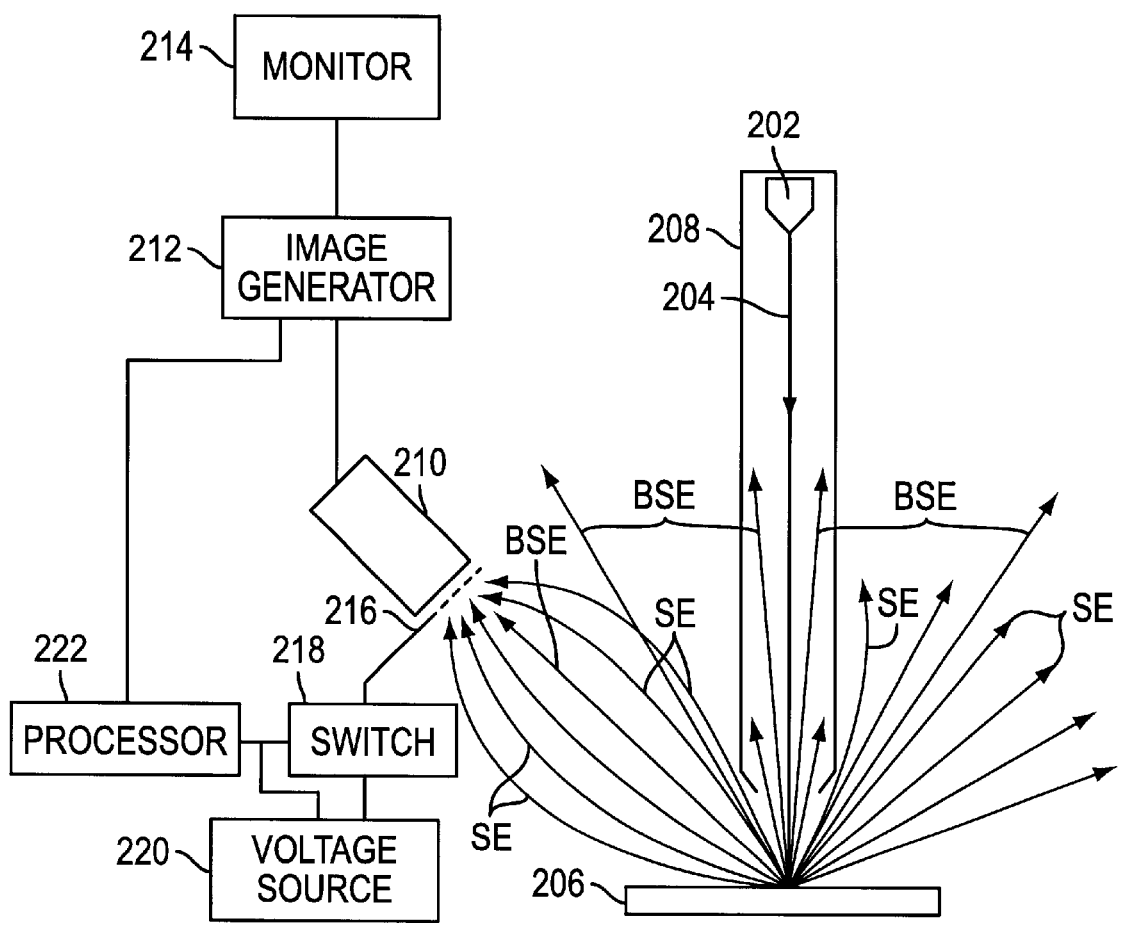
FIGS. 3A and 3B schematically illustrate sequential phases of a method in accordance with the present invention.
Figure 3B:
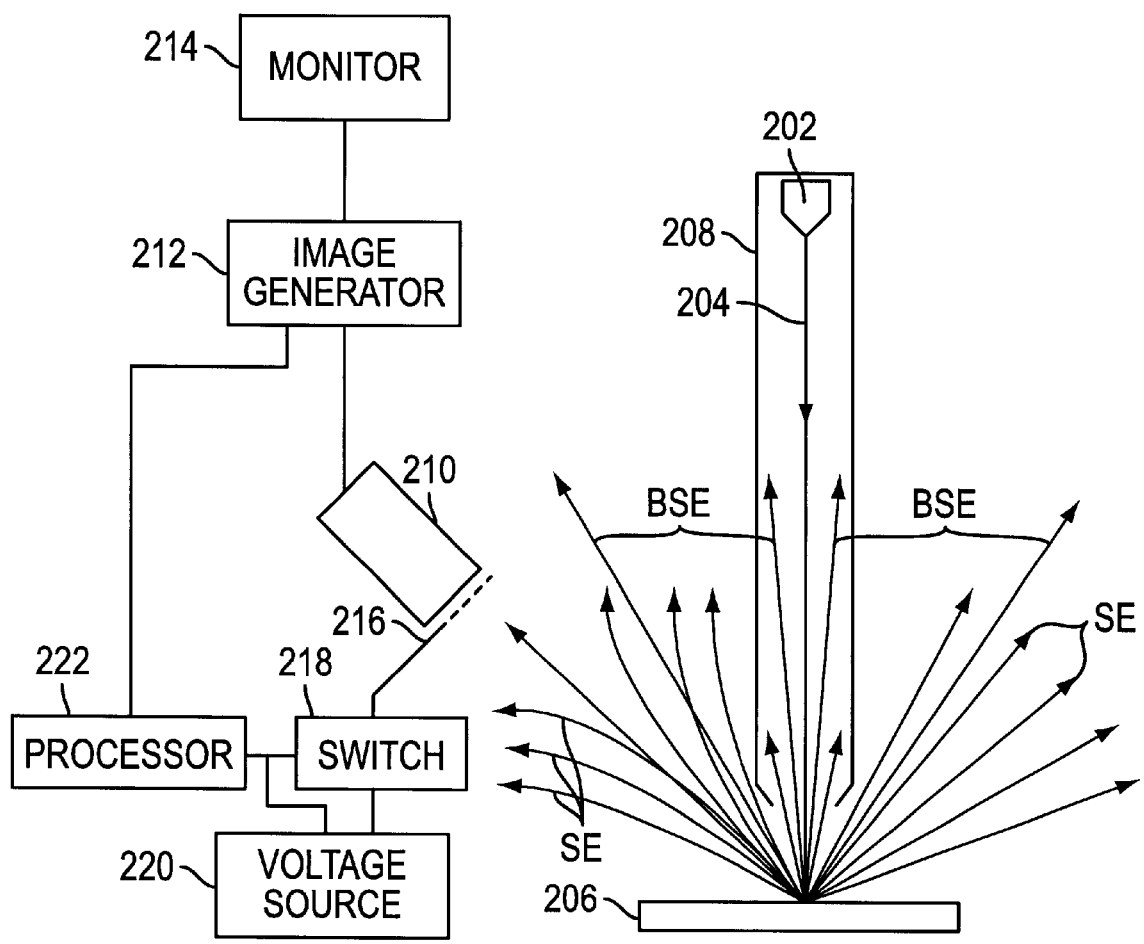
Figure 4:
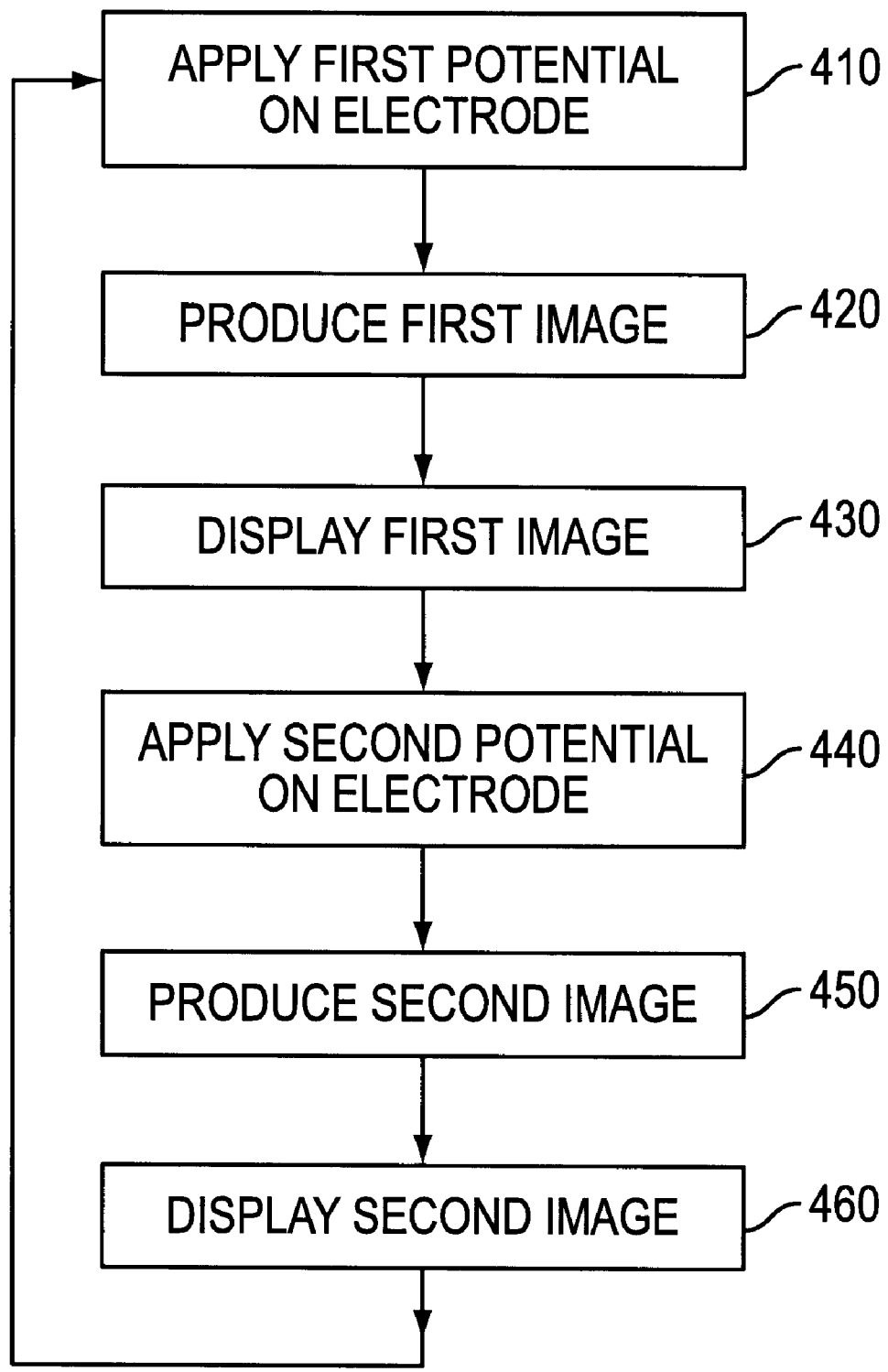
FIG. 4 is a flow chart illustrating a method in accordance with the present invention.

Exemplary modes of operation of the present invention are illustrated in FIGS. 3A and 3B, and the flow chart of FIG. 4. In step 410, processor 222 controls switch 218 and voltage source 220 to apply a first potential on electrode 216 for a given amount of time; e.g., a positive potential of about 50 keV to about 100 keV to attract secondary electrons SE to detector 210, as shown in FIG. 3A. Image generator 212 will then produce a first image from the predominantly secondary electrons SE attracted to detector 210 (step 420) and display the first image on a monitor, such as monitor 214 (step 430).

Next, in step 440, processor 222 controls switch 218 and voltage source 220 to impose a second potential on electrode 216 for a given amount of time; e.g., a negative potential of about 50 eV to about 100 eV to repel secondary electrons SE from detector 210, as shown in FIG. 3B. Image generator 212 will then produce a second image from the predominantly backscattered electrons BSE impinging on detector 210 (step 450) and display the second image on a second monitor, or preferably at a different location on monitor 214 than the first image (step 460). When primary beam 204 impacts specimen 206, more secondary electrons SE are released from specimen 206 than backscattered electrons BSE are deflected. Therefore, if a potential is not imposed on electrode 216 to repeal or attract secondary electrons SE, the resulting image will be produced mostly from secondary electrons SE, and not backscattered electrons BSE.

Steps 410 through 460 are repeated until the user specifies the production of a different image or images; i.e., instructs processor 222 to impose a different potential on electrode 216 to change the characteristics of the first and/or second images. For example, processor 222 can be instructed to impose a negative potential as the first potential and no potential on electrode 216 as the second potential, as shown in FIG. 2, to produce an image different than either of the first or second images described in the proceeding paragraphs. Instructions to processor 222 can be specified in what is referred to as the "reipe" of various parameters and procedures for a particular production run. An application engineer, as the user, prepares the "recipe".

Although the first and second images are produced consecutively, image generator 212 causes monitor 214 (or multiple monitors) to display the first and second images substantially simultaneously by employing well-known graphics techniques. In one such technique, processor 222 alternately imposes the first and second potentials on electrode 216; that is, processor 222 imposes the first potential for a long enough time to collect information for image generator 212 to produce and display the first image, then imposes the second potential for a long enough time to collect information to produce and display the second image. Processor 222 then repeats this process to substantially continuously provide information to image generator 212 to improve and update each successive image. The frequency of alternation of image updating between the two images is preferably performed at a rate too fast to be readily perceptible to a human viewer, who perceives multiple substantially continuous images.

In another technique, processor 222 imposes the first potential on electrode 216 for a significantly longer period of time, to collect enough information to produce a high-quality first image, then applies the second potential for the same amount of time to collect enough information to produce a high-quality second image, then repeats this process if desired by the user. The longer the time periods, the higher the quality of the resultant images.

If a single monitor is used to display both the first and second images simultaneously in a split-screen format, the two images are interleaved by image generator 212 and displayed in a conventional manner, as in prior art defect review SEMs which employ multiple detectors to generate multiple images and display them on a single monitor, such as SEMVision™ available from Applied Materials of Santa Clara, Calif.

Although the above-described embodiment of the invention produces two images of the specimen simultaneously, the invention is not limited to the production of only two images. It is easily adaptable to the production of more than two simultaneous images by providing the appropriate algorithm to processor 222 (to impose more than two consecutive potentials on electrode 216) and image generator 212 (to produce the specified number of images simultaneously). Moreover, if additional detectors 210 and electrodes 216 are provided in different locations, additional images are provided simultaneously from additional perspectives.

Figure 5:
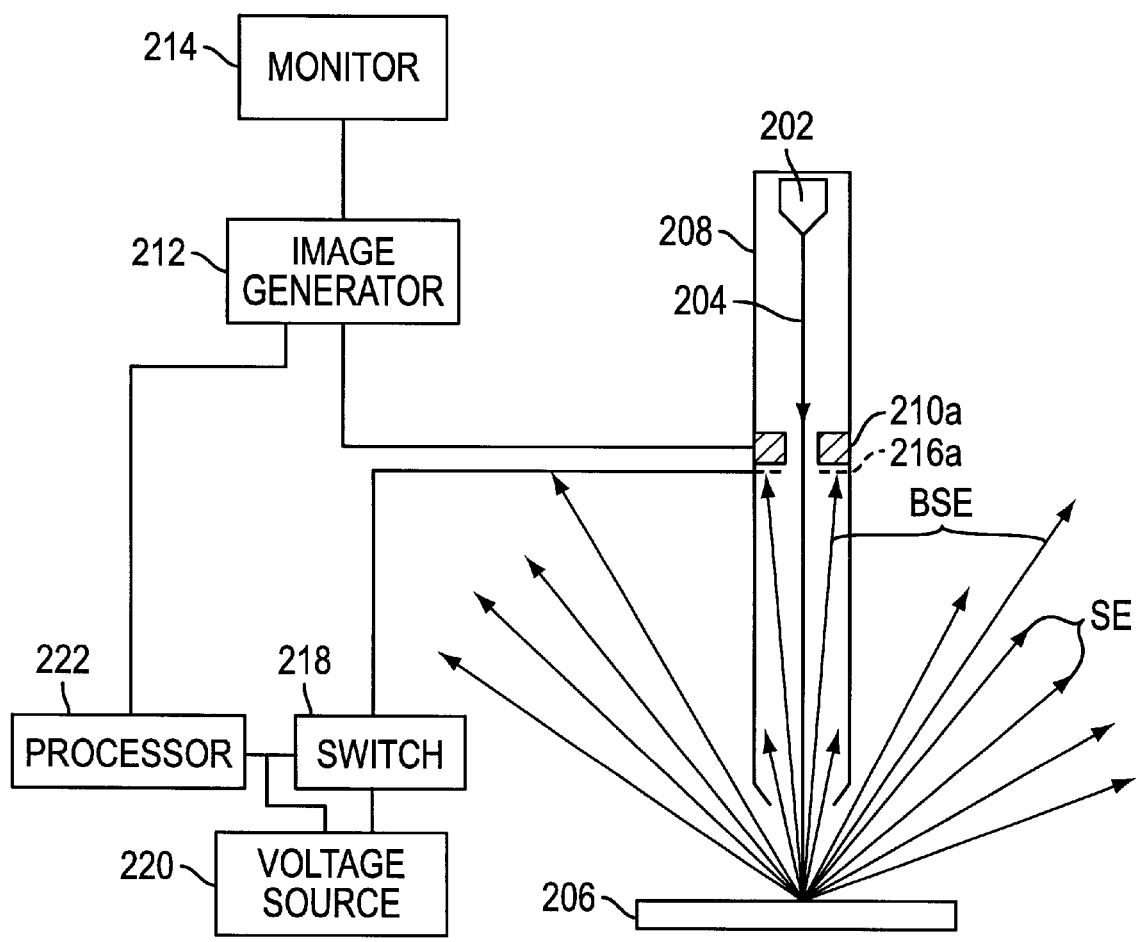
FIG. 5 depicts a SEM according to another embodiment of the present invention.

In another embodiment of the invention, as depicted in FIG. 5, a detector 210a and electrode 216a are located inside optical column 208, rather than outside column 208. The apparatus of FIG. 5 is in all other respects identical to that of the apparatus of FIG. 2.

The inventive defect review SEM enables several images of a location of interest on a semiconductor wafer to be generated simultaneously, each image having different attributes; for example, an image generated from backscattered electrons which is mostly indicative of material characteristics, an image generated from secondary electrons which is mostly indicative of topography, and/or one or more images generated from a mixture of both backscattered and secondary electrons. Thus, many images of defects can be easily compared with each other, images of defect sites and reference sites can be easily compared, and defects can be more readily identified and classified than with conventional defect review SEM's.

The present invention is applicable to the inspection of any semiconductor wafer, and is especially useful for in-process inspection of semiconductor wafers during manufacture of high-density semiconductor devices with submicron design features.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, as one having ordinary skill in the art would recognize, the present invention can be practiced without resorting to the details specifically set forth. In other instances, well known processing structures have not been described in detail, in order not to unnecessarily obscure the present invention.

Only the preferred embodiments of the invention and but a few examples of its versatility are shown and described in the present disclosure. It is to be understood that the invention is capable of use in various other combinations and environments and is capable of changes or modifications within the scope of the inventive concept as expressed herein.

What is claimed is:

1. A particle beam apparatus for imaging of a specimen, the particle beam apparatus comprising:
    a particle source for providing a primary beam for impinging on the specimen to release secondary electrons therefrom and to provide electrons to be backscattered by the specimen;
    a detector for detecting the backscattered and the secondary electrons;
    an electrode chargeable to a plurality of potentials for directing a path of the secondary electrons, the electrode disposed between the detector and the specimen;
    an imager responsive to the detector for generating images based on the secondary electrons and the backscattered electrons; and
    a charge controller for automatically controlling the potential on the electrode such that the imager generates a plurality of different images;
    wherein the imager generates the plurality of different images substantially simultaneously.

2. The apparatus according to claim 1, wherein the electrode is a grid disposed proximal to the detector.

3. The apparatus according to claim 1, wherein the charge controller includes a switch that applies a first potential on the electrode to attract the secondary electrons to the detector such that the imager produces a first image, and applies a second potential on the electrode to repel the secondary electrons such that the imager produces a second image.

4. The apparatus according to claim 3, wherein the charge controller includes a processor that controls the switch to alternate application of the first potential on the electrode to produce the first image, and the second potential on the electrode to produce the second image.

5. The apparatus according to claim 3, wherein the charge controller includes a processor that controls the switch to alternate application of the first potential and the second potential on the electrode to substantially continuously provide information to the imager to produce the first and second images.

6. The apparatus according to claim 3, wherein the first and second potentials have a magnitude about equal to a kinetic energy of the secondary electrons.

7. The apparatus according to claim 1, wherein the charge controller includes a switch that applies a negative potential on the electrode to repel the secondary electrons such that the imager produces a first image, and applies no charge on the electrode such that the imager produces a second image.

8. The apparatus according to claim 1, wherein the imager comprises an image generator for producing the plurality of images and a monitor for displaying the plurality of images.

9. The apparatus according to claim 1, further comprising an optical column that encloses and focuses the primary beam on the specimen, wherein the detector and the electrode are inside the optical column.

10. The apparatus according to claim 1, further comprising an optical column that encloses and focuses the primary beam on the specimen, wherein the detector and the electrode are outside the optical column.

11. A method for imaging a specimen, which method comprises:
    directing a particle beam onto the specimen to release secondary electrons therefrom and to backscatter electrons of the particle beam therefrom;
    detecting the backscattered and the secondary electrons using a single detector having an electrode;
    automatically controlling a charge on the electrode for directing the path of the secondary electrons relative to the detector;
    consecutively producing a plurality of images based on the detected secondary electrons and backscattered electrons; and
    displaying the plurality of images substantially simultaneously.

12. The method according to claim 11, further comprising:
    applying a first potential on an electrode to direct the path of the secondary electrons towards the detector to produce a first image; and
    applying a second potential on the electrode to direct the path of the secondary electrons away from the detector to produce a second image.

13. The method according to claim 12, further comprising applying the first potential on the electrode to produce the first image, and applying the second potential on the electrode to produce the second image.

14. The method according to claim 12, further comprising applying the first potential and the second potential on the electrode to substantially continuously produce the first and second images.

15. The method according to claim 11, further comprising:
    applying a first potential on an electrode to direct the path of the secondary electrons away from the detector to produce a first image; and
    applying a neutral bias on the electrode to produce a second image.

* * * * *